United States Patent
Hanebuchi et al.

(10) Patent No.: US 9,921,047 B2
(45) Date of Patent: Mar. 20, 2018

(54) OPTICAL COHERENCE TOMOGRAPHY DEVICE

(71) Applicant: NIDEK CO., LTD., Gamagori, Aichi (JP)

(72) Inventors: Masaaki Hanebuchi, Aichi (JP); Yasuhiro Furuuchi, Aichi (JP)

(73) Assignee: NIDEK CO., LTD., Aichi (JP)

( * ) Notice: Subject to any disclaimer, the term of this patent is extended or adjusted under 35 U.S.C. 154(b) by 772 days.

(21) Appl. No.: 14/499,735

(22) Filed: Sep. 29, 2014

(65) Prior Publication Data

US 2015/0094978 A1     Apr. 2, 2015

(30) Foreign Application Priority Data

Sep. 30, 2013    (JP) ................................. 2013-205061

(51) Int. Cl.
*H04B 10/07*        (2013.01)
*G01B 9/02*         (2006.01)
(Continued)

(52) U.S. Cl.
CPC .......... *G01B 9/02075* (2013.01); *A61B 3/102* (2013.01); *A61B 5/0066* (2013.01);
(Continued)

(58) Field of Classification Search
CPC ............ G01B 9/02091; G01B 2290/70; G01B 9/02069; G01B 2290/45; G01B 9/02075; A61B 3/102; A61B 5/0066
(Continued)

(56) References Cited

U.S. PATENT DOCUMENTS

2009/0046295 A1    2/2009  Kemp et al.
2009/0244547 A1*  10/2009  Ozawa ............... G01N 21/4795
                                                              356/511
(Continued)

FOREIGN PATENT DOCUMENTS

JP    2010-220774 A    10/2010
JP    2010-533301 A    10/2010
(Continued)

OTHER PUBLICATIONS

Michalina Gora et al.; "Ultra high-speed swept source OCT imaging of the anterior segment of human eye at 200 kHz with adjustable imaging range"; Optics Express; vol. 17; No. 17; Aug. 17, 2009; 15 pages.
(Continued)

*Primary Examiner* — Don N Vo
(74) *Attorney, Agent, or Firm* — Sughrue Mion, PLLC

(57) ABSTRACT

An optical coherence tomography device includes an SS-OCT optical system which includes a wavelength swept optical source which sweeps an emission wavelength, an optical splitter which splits an interference signal light caused by interference between a measurement light and a reference light into a first interference signal light and a second interference signal light having a phase difference from the first interference signal light, a balance detector which includes a first detector configured to detect the first interference signal light and a second detector configured to detect the second interference signal light, and which processes detection signals from the first and second detectors to perform balance detection, and an optical member which is disposed between the optical splitter and one of the first detector and the second detector to generate a fixed pattern noise by one of the first interference signal light and the second interference signal light.

15 Claims, 3 Drawing Sheets

(51) Int. Cl.
*A61B 3/10* (2006.01)
*A61B 5/00* (2006.01)

(52) U.S. Cl.
CPC ..... *G01B 9/02004* (2013.01); *G01B 9/02069* (2013.01); *G01B 9/02091* (2013.01); *G01B 2290/25* (2013.01); *G01B 2290/45* (2013.01); *G01B 2290/70* (2013.01)

(58) Field of Classification Search
USPC .......................................................... 398/203
See application file for complete search history.

(56) References Cited

U.S. PATENT DOCUMENTS

| | | | |
|---|---|---|---|
| 2009/0251704 A1* | 10/2009 | Masuda | A61B 5/0066 356/477 |
| 2011/0228280 A1 | 9/2011 | Schmitt et al. | |
| 2012/0013909 A1* | 1/2012 | Podoleanu | A61B 3/102 356/451 |
| 2012/0170046 A1 | 7/2012 | Flanders | |
| 2012/0327423 A1 | 12/2012 | Hanebuchi | |
| 2013/0208968 A1 | 8/2013 | Hanebuchi et al. | |

FOREIGN PATENT DOCUMENTS

| | | |
|---|---|---|
| JP | 2011-196771 A | 10/2011 |
| JP | 2013-512441 A | 4/2013 |
| JP | 2013-148482 A | 8/2013 |
| JP | 2013-156229 A | 8/2013 |

OTHER PUBLICATIONS

Shuichi Makita et al.; "Full-range, high-speed, high-resolution 1-μm spectral-domain optical coherence tomography using BM-scan for volumetric imaging of the human posterior eye"; Optics Express; vol. 16; No. 12; Jun. 9, 2008; 15 pages.

Communication dated Sep. 13, 2016, issued by the Japanese Intellectual Property Office in counterpart Japanese Patent Application No. 2013-205061.

Furukawa, et al.; "Full-Range Imaging of Eye Accommodation by High-Speed Long-Depth Rage Optical Frequency Domain Imaging"; Dec. 1, 2010; vol. 1 No. 5; Biomedical Optics Express; pp. 1491-1501.

Braaf; et al.; "Phase-Stabilized Optical Frequency Domain Imagin AT 1-UM for Measurement of Blood Flow in Human Choroid"; Oct. 24, 2011; vol. 19 No. 220, Optics Express; pp. 20886-20902.

Jung et al.; "Simple Spectral Calibration Method and Its Application Using an Index Array for Swept Source Optical Coherence Tomography "; Journal of the Optical of Korea; vol. 15 No. 4, Dec. 2011; pp. 386-393.

Potsaid, et al.; "Ultrahigh Speed 1050NM Swept Source / Fourier Domain OCT Retinal and Anterior Segment Imaging AT 100,00 to 400,000 Axial Scans Per Second"; Sep. 13, 2010, vol. 18 No. 19, Optics Express; pp. 20029-20048.

Extended European Search Report dated Mar. 12, 2015, by the European Patent Office in related Application No. 14186899.2.

* cited by examiner

US 9,921,047 B2

OPTICAL COHERENCE TOMOGRAPHY DEVICE

CROSS-REFERENCE TO RELATED APPLICATION

This application claims priority from Japanese Patent Application No. 2013-205061, filed on Sep. 30, 2013, the entire subject matter of which is incorporated herein by reference.

TECHNICAL FIELD

The present disclosure relates to an optical coherence tomography device which obtains internal information of an examination object (for example, an eye).

BACKGROUND

As an example of optical coherence tomography (OCT), there has been known a swept source-OCT (SS-OCT) using a wavelength swept optical source. The SS-OCT temporally changes an emission wavelength using the wavelength swept optical source and detects by an optical detector a spectrum including a reflected light from an examination object and a reference light. A spectral signal output from the optical detector is converted into depth information by Fourier analysis.

Incidentally, since a wavelength (wavenumber) change by the wavelength swept optical source does not necessarily occur in proportion to time, there is a possibility that the wavenumber (k) and a depth (Z) may not have a proportional relationship in Fourier transform processing. As a result, an OCT signal which includes a depth profile deviated from a true depth profile may be obtained.

As a solution to this problem, an interferometer is separately provided in addition to the OCT interference optical system, and mapping data on a wavenumber is generated (see Non-Patent Document 1: "Ultra high-speed swept source-OCT imaging of the anterior segment of human eye at 200 kHz with adjustable imaging range", Michalina Gora, Optics Express, Vol. 17, No. 17). In a spectrum domain OCT (SD-OCT), a gold mirror placed on a measurement optical path is imaged multiple times, and mapping data on a wavenumber is generated using the signals (see Non-Patent Document 2: "Full-range, high-speed, high-resolution 1-µm spectral-domain optical coherence tomography using BM-scan for volumetric imaging of the human posterior eye", Shuichi Makita, Optics Express, Vol. 16, No. 12).

However, in the method of Non-Patent Document 1, the separate interferometer is needed. Further, even though data generated by using the gold mirror as in Non-Patent Document 2 is used, it is necessary to acquire data at a different measurement time from the original measurement time. Therefore, it is not possible to cope with an influence of temporal fluctuation in the original measurement.

SUMMARY

Accordingly, the present disclosure provides an optical coherence tomography device which solves at least one of the technical problems in the above technique.

According to an illustrative embodiment of the present invention, there is provided an optical coherence tomography device comprising:

an SS-OCT optical system which includes a wavelength swept optical source configured to sweep an emission wavelength;

an optical splitter which is configured to split an interference signal light caused by interference between a measurement light and a reference light into a first interference signal light and a second interference signal light having a phase difference with respect to the first interference signal light;

a first balance detector which includes a first detector configured to detect the first interference signal light and a second detector configured to detect the second interference signal light, and which is configured to process detection signals from the first detector and the second detectors to perform balance detection; and a first optical member which is disposed between the optical splitter and one of the first detector and the second detector to generate a fixed pattern noise by one of the first interference signal light and the second interference signal light.

BRIEF DESCRIPTION OF THE DRAWINGS

The above and other aspects of the present disclosure will become more apparent and more readily appreciated from the following description of illustrative embodiments of the present disclosure taken in conjunction with the attached drawings, in which.

DETAILED DESCRIPTION

Figure 1:
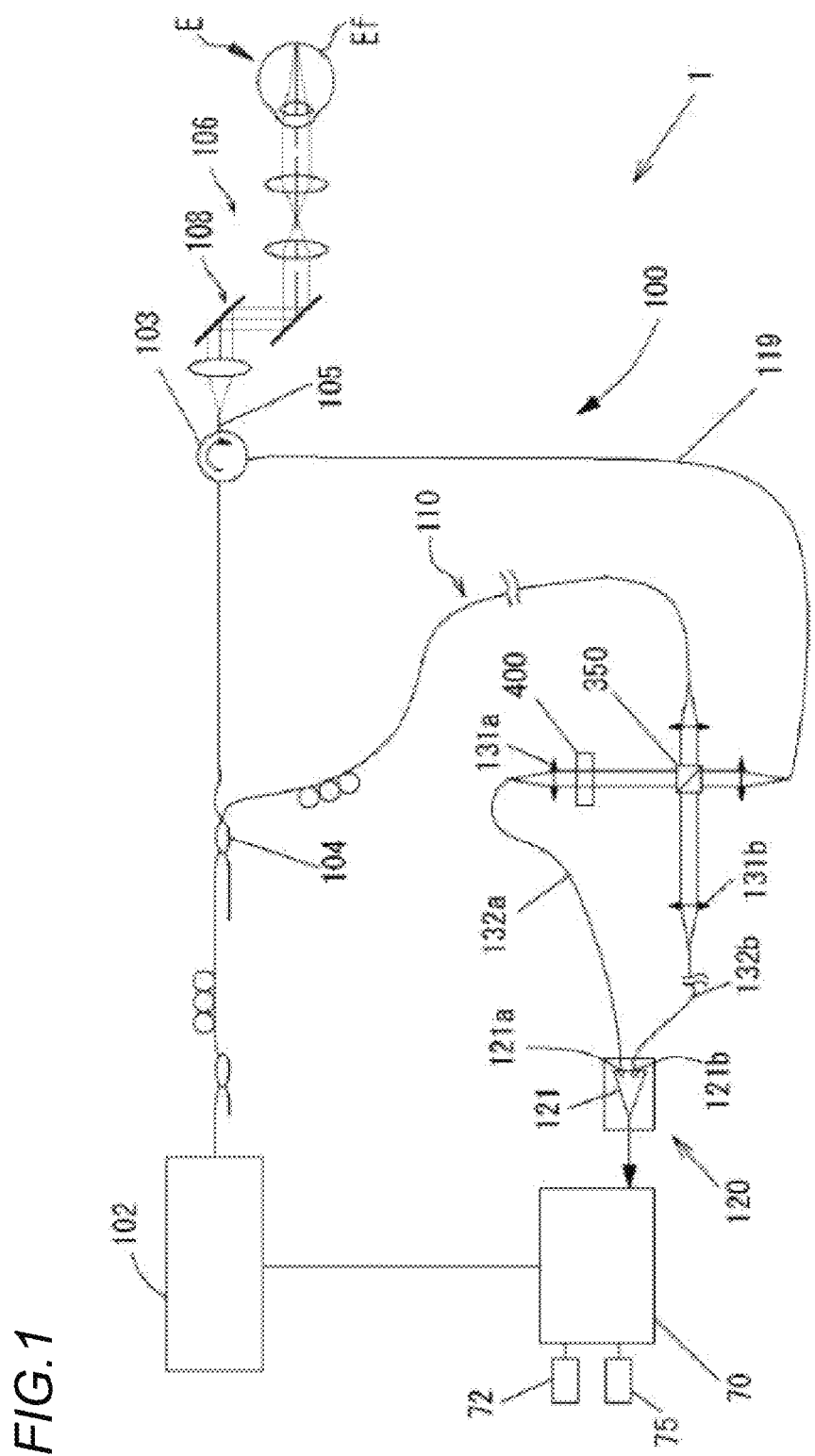
FIG. 1 is an explanatory view showing a configuration of an optical coherence tomography device according to an illustrative embodiment of the present disclosure.

Illustrative embodiments of the present disclosure will be described with reference to the drawings. FIGS. 1 to 5 are drawings related to illustrative embodiments of the present disclosure.

<Overview>

An SS-OCT device 1 according to the present illustrative embodiment obtains correction information for correcting a mapping state of a wavenumber component for each sampling point in a balance detector 121 by calculation based on a signal component corresponding to a fixed pattern noise included in a detection signal output from the balance detector 121. The obtained correction information is used when internal information of an examination object is obtained based on an interference signal at each wavenumber.

<Basic Configuration>

The SS-OCT device 1 employs an SS-OCT as a basic configuration. The SS-OCT device 1 includes an interference optical system (OCT optical system) 100 and a calculation controller (calculation processor) 70. The system of this SS-OCT device 1 may be applied to a standard OCT for detecting a reflection intensity of the examination object, and further, to a polarization sensitive OCT (PS-OCT) and to a Doppler OCT for detecting a phase state of the examination object (for example, amount of phase shifting). Further, the system of this SS-OCT device 1 may be applied to a multi-function OCT in which the PS-OCT and Doppler OCT are combined.

The interference optical system 100 employs an SS-OCT optical system using a wavelength swept optical source (for example, optical source 102) which temporally sweeps an emission wavelength. The SS-OCT device 1 performs sampling of an interference signal between a measurement light and a reference light in accordance with the emission wavelength change by the wavelength swept optical source, and obtains internal information of the examination object based on the interference signal at each wavelength obtained by the sampling.

The interference optical system 100 has a configuration related to an interferometer for obtaining a tomographic image of the examination object using OCT processing. The interference optical system 100 includes a splitter (optical splitter), a measurement optical path, a reference optical path, a combiner (optical combiner), and an optical detector (hereinafter, detector) 120. The splitter (for example, coupler 104) splits a light from the wavelength swept optical source into the measurement optical path and the reference optical path. Examples of the splitter and the combiner may be a beam splitter, a half-mirror, a fiber coupler, a circulator, or the like. The measurement optical path has a configuration for guiding the light to the examination object. The reference optical path has a configuration for allowing the light to proceed in the device to interference with the measurement light. The combiner combines (causes interference between) the measurement light from the measurement optical path, which is reflected from the examination object, and the reference light from the reference optical path. An optical scanner 108 is disposed on the measurement optical path and is used for scanning over the examination object with the measurement light.

The optical splitter (for example, beam splitter 350, coupler 450) splits an interference signal light produced by the interference between the measurement light and the reference light into a first interference signal light and a second interference signal light which has a phase difference with respect to the first interference signal light. The optical splitter is disposed on an optical path downstream from a position where the interference between the measurement light and the reference light occurs.

<Balance Detector>

The detector 120 receives the interference signal light produced by the interference between the measurement light and the reference light. The balance detector 121 is used as the detector 120 in the present illustrative embodiment. The balance detector 121 includes a first detector 121*a* for detecting the first interference signal light and a second detector 121*b* for detecting the second interference signal light. The balance detector 121 is used to perform processing of detection signals from the first detector 121*a* and the second detector 121*b* to perform the balance detection.

<Pattern Noise Generating Member>

An optical member (for example, a cover glass 400) is disposed between one of the first detector 121*a* and the second detector 121*b* and the optical splitter (for example, beam splitter 350 or coupler 450) to generate a fixed pattern noise using one of the first interference signal light and the second interference signal light. Such an optical member may be disposed such that a front surface and a rear surface of the optical member each vertically intersect with an optical axis.

The optical member may be disposed on one of the first detector 121*a* side and the second detector 121*b* side, which has a higher light splitting ratio by the optical splitter (for example, beam splitter 350 or coupler 450). In this case, a signal intensity unbalance between the first detector 121*a* and the second detector 121*b* may be decreased.

<Calculation Processing>

The calculation controller 70 can perform at least one of control processing of respective components of the device, image processing and calculation processing. For example, the calculation controller 70 obtains a detection signal from the detector 120. The calculation controller 70 obtains a spectral signal including the interference signal light at each wavelength, and performs processing of the spectral signal. The calculation controller 70 performs the processing of the spectral signal and obtains the internal information of the examination object (for example, data (depth information) of the examination object in a depth direction).

Further, the calculation controller 70 may arrange the internal information obtained from different positions by scanning or the like with the measurement light in order to obtain information (for example, shape information, polarization properties, or the like) of the examination object. The calculation controller 70 stores the obtained results in a memory 72. The calculation controller 70 may display the obtained results on a monitor 75 (image display unit).

The spectral signal (spectral data) is converted into a function I(k) which is equally spaced with respect to a wavenumber k ($=2\pi/\lambda$(wavelength)). The calculation controller 70 performs Fourier transform of the spectral signal in a wavenumber k-space, thereby obtaining a signal distribution in a depth (Z) region.

According to the present illustrative embodiment, the calculation controller 70 obtains the correction information for correcting a mapping state of a wavenumber component for each sampling point in the balance detector 121 by calculation based on a signal component corresponding to a fixed pattern noise (FPN) included in a detection signal output from the balance detector 121.

The calculation controller 70 may correct a corresponding relationship between each wavelength component and each sampling point using the obtained correction information, and may obtain the internal information of the examination object using the corrected corresponding relationship. The calculation controller 70 may obtain correction information for each spectral signal obtained at a predetermined frame rate, and may obtain the internal information using the obtained correction information.

Information after performing the Fourier transform is represented as a signal including a real component and an imaginary component in a Z space. In a case of obtaining information on shape, the calculation controller 70 obtains the absolute value of the real component and the imaginary component from the signal in the Z space, thereby obtaining an A scan signal (signal intensity value in the depth direction). The calculation controller 70 can arrange the A scan signals obtained at different positions, and can obtain a tomographic shape image of the examination object.

The examination object may be a living body, such as an eye (anterior eye part, fundus, or the like), skin, or may be a material other than the living body.

<Phase Shift of Spectral Signal>

The calculation controller 70 may correct a phase shift of the spectral signal which includes an interference signal at each wavelength, using the fixed pattern noise from the pattern noise generating member. As described above, the calculation controller 70 may correct the mapping state of the wavenumber component for each sampling point after correction of the phase shift.

For example, regarding the phase shift of the spectral signal, the calculation controller 70 performs processing of the A scan signal and obtains a depth position of the fixed pattern noise, and obtains the phase information of the spectral signal corresponding to the obtained depth position. The depth position of the fixed pattern noise corresponds to a depth position of the interference component generated by the pattern noise generating member.

Specifically, the calculation controller 70 may detect a phase φ (Z0) of the spectral signal at an FPN detecting position based on F(Z0) at a depth position (FPN detecting position) Z0 where the FPN is detected. The phase φ(Z0) is a function in which the abscissa is the wavenumber k and the ordinate is the phase φ. For example, the phase φ(Z0) is obtained from the arctangent of a ratio between a real part RealF(Z0) and an imaginary part ImagF(Z0) of a Fourier transform value F(Z0) at the FPN detection position Z0. Here, the arctangent of a ratio between the real part and the imaginary part of the Fourier transform value is calculated by the arctangent processing, and the phase φ is obtained.

Subsequently, the calculation controller 70 performs the correction processing of the Fourier transform value F(Z) for each A scan based on the phase φ of the acquired FPN detection position Z0 such that the phase shift (amount of position shifting) of an interference signal f(k) is removed (for the detailed method, see JP-A-2013-156229).

EXAMPLE

In an example to be described later, the SS-OCT device 1 shown in FIG. 1 is used as the optical coherence tomography device, and the examination object is an fundus of an eye.

The SS-OCT device 1 employs the swept source-OCT (SS-OCT) as a basic configuration and includes a wavelength swept optical source (wavelength variable optical source) 102, the interference optical system (OCT optical system) 100 and the calculation controller (calculation processing device) 70. Further, the SS-OCT device 1 includes the memory 72, the monitor 75 and a frontal view observation system (not shown) and a fixation target projection system (not shown). The calculation controller (hereinafter, controller (control unit)) 70 is connected to the optical source 102, the interference optical system 100, the memory 72 and the monitor 75.

The interference optical system 100 employs a swept source-OCT (SS-OCT) method. The wavelength swept optical source (wavelength scanning-type optical source) is used as the optical source 102. The optical source 102 temporally changes the emission wavelength at high speed.

In a case of the wavelength swept optical source, the optical source 102 is configured by a laser medium, a resonator and a wavelength selecting filter. The wavelength selecting filter may be a filter, in which a diffraction grating and a polygonal mirror are combined or a filter using a Fabry-Perot etalon.

According to the present example, a tunable laser of AXSUN technologies, Inc. is used as the optical source which has a narrow instantaneous line width and a short resonator length (for example, λc=1060 nm, Δλ=110 nm, δλ=0.055 nm, resonator length ~14 mm) This kind of wavelength swept optical source is disclosed in U.S. Patent Application Publication No. 2009/0059971, for example.

The coupler (splitter) 104 splits a light emitted from the optical source 102 into a measurement light and a reference light. A circulator 103 guides the light from the coupler 104 to an optical fiber 105, and then guides the light from the optical fiber 105 to an optical fiber 119. Incidentally, the circulator 103 may be a coupler.

The interference optical system 100 guides the measurement light to a fundus Ef of an eye E by a measurement optical system 106. The interference optical system 100 guides the reference light to a reference optical system 110. The interference signal light is obtained by interference between the measurement light reflected from the fundus Ef and the reference light. The interference optical system 100 causes the detector (optical detector) 120 to receive the obtained interference signal light.

The optical fiber 105, an optical scanner 108 and an objective lens system are provided in the measurement optical system 106 in this order. The measurement light is directed to the optical scanner 108 through the circulator 103 and the optical fiber 105. The reflection direction of the measurement light is changed by the optical scanner 108. The light deflected by the optical scanner 108 becomes a parallel beam by the objective lens system and is incident to the eye E and to the fundus Ef.

The optical scanner 108 causes the measurement light to scan the fundus Ef in an XY direction (transverse direction). The optical scanner 108 is disposed at a position where the optical scanner and a pupil have a substantial conjugate relationship with each other. The optical scanner 108 may include two galvano-mirrors, a reflection angle of which is adjusted arbitrarily by a drive mechanism.

The light flux emitted from the optical source 102, which the reflection (proceeding) direction is changed, is used to scan the fundus in an arbitrary direction. As well as a reflective mirror (galvano-mirror, polygonal mirror, or resonant scanner), an acousto-optic member (AOM) which changes the proceeding (deflection) direction of a light may be used as the optical scanner 108.

The controller 70 controls the driving of the optical scanner 108 such that the scanner performs scanning with the measurement light in a direction (transverse direction) perpendicular to the depth direction of the fundus Ef. Of each measurement light, a backscattered light (reflected light) from the fundus Ef reaches the beam splitter 350, through the objective lens system, the optical scanner 108, the optical fiber 105, the circulator 103 and the optical fiber 119. The backscattered light is multiplexed and interferes with the reference light in the beam splitter 350.

The reference optical system 110 produces the reference light to be combined with the reflection light which is obtained by the reflection of the measurement light on the fundus Ef. The reference optical system 110 may be of a Michelson or Mach-Zehnder type. According to the present example, the reference optical system 110 is configured as a transmissive optical system (for example, optical fiber) and guides the light from the coupler 104 to the detector 120 not by turning back but by transmitting the light. The reference optical system 110 may be configured as a reflective optical system (for example, reference mirror), and may cause the light from the coupler 104 to turn back to the coupler 104 by reflection of the light through the reflective optical system to guide the light to the detector 120.

The device of the present example causes at least a part of the optical member disposed in the interference optical system 100 to move in the optical axis direction in order to adjust a difference in length between the optical paths of the measurement light and the reference light. For example, the reference optical system 110 has a configuration in which the optical member in the reference optical path is moved, thereby adjusting the difference in length between the optical paths of the measurement light and the reference light. The configuration for changing the difference in length between the optical paths may be disposed in the measurement optical path. For example, the optical member (for example, end of the optical fiber) disposed in the measurement optical path may move in the optical axis direction.

The beam splitter 350 splits the interference signal light into multiple (two in the present example) lights (two in the present example). The cover glass 400 and the first detector 121a are disposed in one of the optical paths split by the beam splitter 350, and the second detector 121b is disposed in the other optical path.

The first detector 121a and the second detector 121b detect the interference signal light split by the beam splitter 350, and the balance detector 121 performs the balance detection. An interference signal from the first detector 121a and an interference signal from the second detector 121b have a 180-degree phase difference. The balance detector 121 includes a circuit in which the detection signals from the first and second detectors 121a and 121b are processed, and obtains a difference between the interference signal from the first detector 121a and the inverse-processed interference signal from the second detector 121b, thereby being capable of suppressing a direct current (DC) component.

Each of the detectors 121a and 121b are a point sensor which includes only one light receiving unit, and an avalanche photodiode may be used as the detector. The detectors 121a and 121b may be arranged to be spaced from each other.

One of the lights split by the beam splitter 350 is received by the first detector 121a through the cover glass 400, a first optical fiber 131a, and a first collective lens 132a. The other of the lights split by the beam splitter 350 is received by the second detector 121b through a second optical fiber 131b and a second collective lens 132b.

The cover glass 400 is used as the optical member for producing an interference light for calibration using one of the lights split by the beam splitter 350.

The cover glass 400 has a known thickness d. The cover glass 400 is disposed such that the front surface and the rear surface thereof each vertically intersect with an optical axis L3. The interference signal light which passes through the cover glass 400 is split into a transmissive light which is transmitted through the cover glass 400 one time, and an internal reflection light which is reflected inside the cover glass 400 2m (m=1, 2, 3 . . . ) times and passes through the cover glass (see FIG. 2). The transmissive light and the internal reflection light interfere with each other, so that the interference light is produced.

The interference light produced by the cover glass 400 is detected as the fixed pattern noise by the first detector 121a. A peak of the light which is directly transmitted through the cover glass 400 and a peak of the light which is reflected twice inside the cover glass 400 and passes through the cover glass are detected to be separated by 2m times the thickness (2md) of the cover glass 400.

In the present example, the cover glass 400 is disposed between the beam splitter 350 and the first detector 121a. However, the cover glass 400 may be disposed between the beam splitter 350 and the second detector 121b.

Between the first detector 121a and the second detector 121b, the cover glass 400 may be disposed to a detector side to which a more intense light is guided. In a case where the light is split by the beam splitter 350 (alternatively, the coupler 450 to be described later), there is a possibility that the light is split not by 50 to 50, and the intensities are unbalanced. The cover glass is disposed on the detector side to which the more intense light is guided, thereby attenuating the light using the cover glass 400 and decreasing the balance difference between the intensities.

The reason why the cover glass 400 is disposed on one detector side of the balance detector 121, but not on the other detector side of the balance detector is that the interference component due to the cover glass remains in the detection signal when the DC current is removed by the balance detector 121. That is, in a case where the cover glasses with an equal thickness are disposed on both detector sides, the interference components of both detector sides are offset against each other as DC components, and are removed from the detection signals, and it is difficult to perform the calibration. That is, the inventor of this disclosure has found that it is possible to include the interference component for calibration in the interference signal by causing the light passing through the cover glass 400 to be incident to one of the first detector 121a and the second detector 121b.

The configuration of the optical member is not limited to the above configuration, and optical members which have different thicknesses may be disposed on both detectors of the balance detector 121 such that different fixed pattern noises are produced. In this case, signals with two frequencies are included in the interference signal as the fixed pattern noise. For example, the calibration is performed preferentially using the signal which has a lower frequency, thereby improving the correction accuracy.

Incidentally, in the present example, the cover glass 400 is disposed to be fixed in the optical path. However, the cover glass 400 may be insertable/removable with respect to the optical path, and may be inserted into the optical path, as necessary.

When the emission wavelength is changed by the optical source 102, the corresponding interference signal light is received by the balance detector 121. As a result, the interference signal light at each wavelength is received by the balance detector 121 as a spectral light. The first detector 121a and the second detector 121b detect the interference signal light at a predetermined sampling rate. In this case, the number of sampling points is set corresponding to the sampling rate. Since the optical source 102 temporally changes the emission wavelength, each sampling point by the balance detector 121 forms a pair with each emission wavelength (wavenumber) of the optical source 102. The interference signal at each wavelength output from the balance detector 121 is transmitted to the calculation controller 70 as the spectral signal. The depth profile is formed based on the obtained spectral signal.

The calculation controller 70 controls the driving of the optical scanner 108 such that the scanner performs scanning on the fundus Ef with the measurement light in the transverse direction. The calculation controller 70 arranges the depth profiles of scanning positions in order and forms a fundus tomographic image.

Hereinafter, an example of a case where a mapping state (wavenumber sampling mapping) of each wavelength component (wavenumber component) with respect to the sampling point p is corrected based on a calibration component by the cover glass 400 is described.

Figure 2:
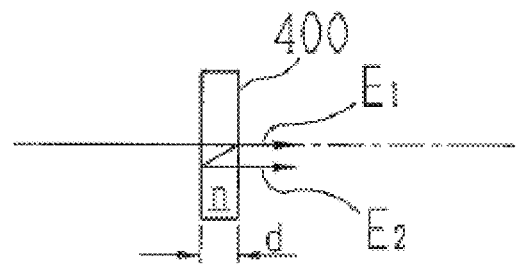
FIG. 2 is a view showing interference of light flux incident to a cover glass which is used for calibration.

As shown in FIG. 2, when the light for calibration passes through the cover glass 400, the light is split into multiple lights including a first component E1 (directly transmitted light flux) which is transmitted through the cover glass 400 and a second component E2 (light flux reflected one time on the rear surface and one time on the front surface) which is reflected two times inside the cover glass 400, and is received by the first detector 121*a*.

The spectral signal obtained in the balance detector 121 has information on the light for calibration, which is interfered by the cover glass 400. A refractive index n and the thickness d of the cover glass 400 are known in advance. In the present example, the thickness d is smaller than the measurement range of the interference optical system 100.

The wavelength λ of the light flux for calibration, which is detected in the balance detector 121, is represented by the following equation (1).

$$\lambda = 1e^{-9}(A + Bp + Cp^2 + Dp^3) \quad (1)$$

Here, it is considered that C=D=0 by a first approximation, and A=λ0 (central wavelength of the optical source). A value of B is determined such that an estimated wavelength width (for example, design value) is satisfied. Here, p is a sampling point in the detector, and an intermediate value in a sampling range of one-time wavelength sweeping is set to 0. For example, when the sampling number in the present example is 2048 points, p is a value from −1024 to 1023.

Subsequently, a linear k-space (k is the wavenumber) is obtained to have equal spacing, and an interference intensity I(k) is obtained based on data which is zero padded an even number of times (in the present example, four times). A fast Fourier transform (FFT) related to k is applied to I(k), and 2nd=z(peak) is obtained from a peak corresponding to two times the optical thickness nd of the cover glass. After extracting only the positive frequency component, the inverse fast Fourier transform (IFFT) is performed, and a phase φ(k) is obtained from the real and imaginary parts thereof.

Since the interference light to be received by the first detector 121*a* is produced from interference between the first component E1=E0exp(ikz) which is directly transmitted through the cover glass 400 and the second component E2=rE0exp(ik (z+2nd)) in which the phase is delayed by the reflection two times in the cover glass 400 (where r is a total reflectance of the cover glass), an intensity distribution I(k) is represented by the following equation (2).

$$I(k) = |E_1 + E_2|^2 = (1 + r^2)E_0^2 + rE_0^2(\exp(ik2nd) + \exp(-ik2nd)) = \quad (2)$$
$$(1 + r^2 + 2r\cos(k2nd))E_0^2$$

The above described phase φ(k) means that exp(ik2nd) is taken out from the equation (2) and the phase is obtained. When the wavenumber sampling mapping is perfect in the spectral signal which is changed by the wavelength swept optical source, φ(k) forms a straight line as shown in the following equation (3).

$$\varphi(k) = 2ndk = z(\text{peak})k \quad (3)$$

However, when the wavenumber mapping is not perfect, φ(k) does not form a straight line.

Here, z(peak) is obtained as follows. The interference component can be generalized as exp(ikz), and k and z have a relationship of kz=2π. Here, z can be represented by the following equation (4), in which N is a sampling point number and kmax and kmin are maximum/minimum values of k value detected at each sampling point.

$$z = \frac{2\pi \cdot i}{k\max - k\min} \quad (4)$$

Here i=0, 1, 2, . . . , N/2.

When the interference signal corresponding to z(peak) is detected at an i(peak)-th sampling point, z(peak) can be represented as the following equation (5).

$$z(\text{peak}) = \frac{2\pi \cdot i(\text{peak})}{k\max - k\min} \quad (5)$$

φ(k) ideally forms a straight line of which a slope is z(peak) and an intercept is 0. When a quadratic or cubic non-linear term is σ, k is corrected by the following equation (6).

$$k' = k + \frac{\sigma}{z(\text{peak})} \quad (6)$$

A corrected wavelength λ' is determined to λ'=2π/k'.

Here, when σ is expanded by the following expression (7), σ is a non-linear term, σ=b2k²+b3k³.

$$\phi(k) = \sum_{i=0}^{3} b_i k^i \quad (7)$$

Figure 3:
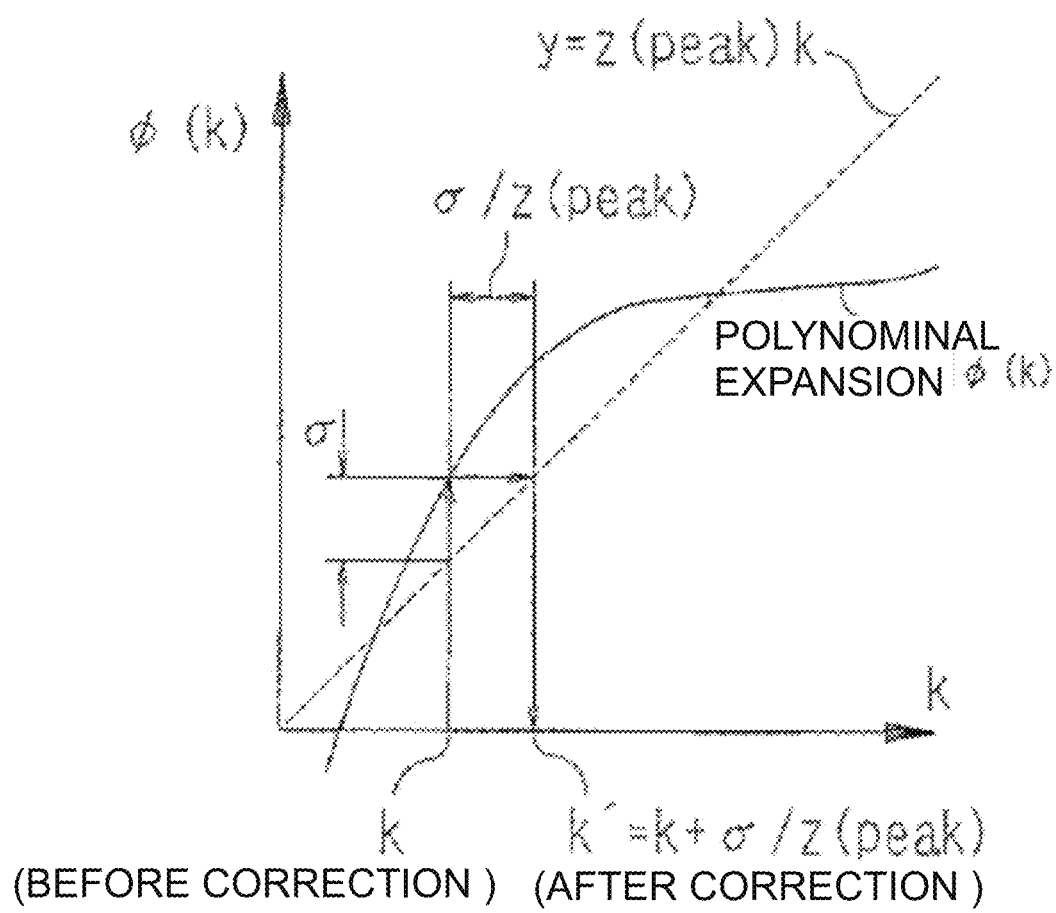
FIG. 3 is a graph schematically showing a correction process of wavenumber mapping.

FIG. 3 is a view schematically showing the mapping of the spectral signal to be corrected by performing a correction calculation. It is determined that the values are convergent when the values of the corrected φ(kmin) and φ(kmax) are present in a predetermined acceptable range (for example, approximately 1E⁵) from the ideal values, z(peak)·kmin and z(peak)·kmax. When this condition is not satisfied, a similar calculation is repeated using the corrected λ' described above.

That is, the calculation controller 70 obtains the correction information by calculation from the spectral signal which is obtained in the balance detector 121 and stores the obtained correction information in the memory 72. Accordingly, a corresponding relationship between each wavelength component detected in the balance detector 121 and each sampling point is more accurately obtained.

According to the above-described configuration, it is possible to optimize the wavenumber mapping in the SS-OCT, using a simple configuration of the device without providing a complex optical system or circuit system.

Figure 4:
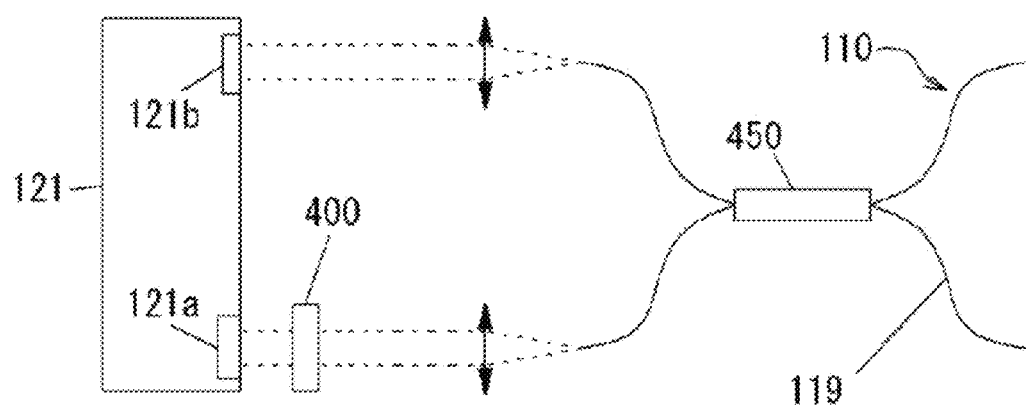
FIG. 4 is an explanatory view showing a configuration of an optical coherence tomography device according to a first modified example of the present disclosure.

In the above-described configuration, the interference signal light is split by the beam splitter 350, but the configuration is not limited thereto. For example, as shown in FIG. 4, the interference signal light may be split by the coupler 450.

Figure 5:
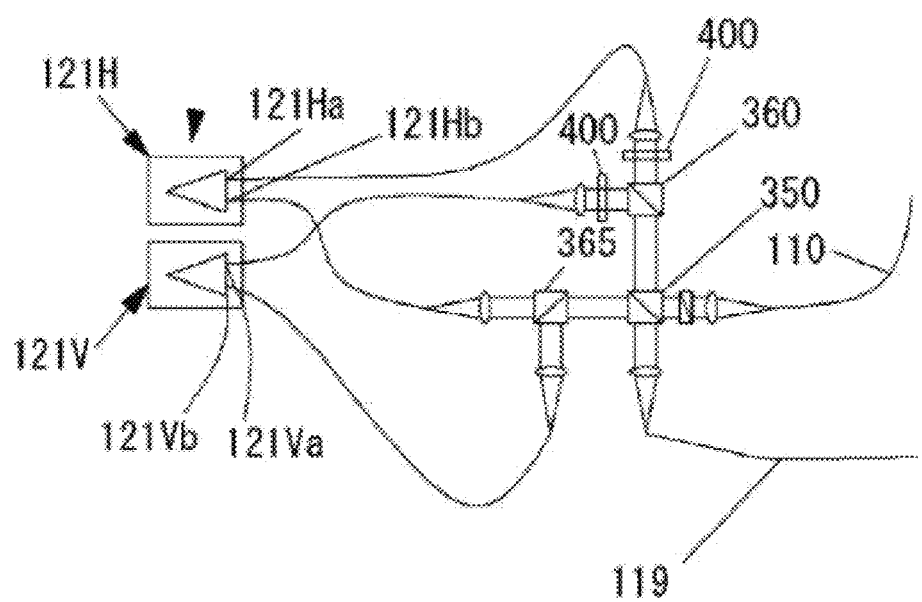
FIG. 5 is an explanatory view showing a configuration of an optical coherence tomography device according to a second modified example of the present disclosure.

Further, in a case of two-channel detection, the cover glass 400 may be disposed on one detector side in each channel (see FIG. 5). In this case, as shown in FIG. 5, the cover glass 400 may be disposed in each optical path on one detector side in each channel. Alternatively, the cover glass 400 may be disposed on a common optical path (for example, between beam splitter 350 and polarization beam splitter) on one detector side in each channel. The two-channel detection may be applied to polarization sensitive SS-OCT (for a detail, for example, see JP-A-2013-148482). The two-channel detection may be applied to dual beam SS-OCT (OCT which simultaneously images two regions on the fundus), dual beam Doppler SS-OCT (OCT which causes a delay to occur between beams and obtains a Doppler signal), full range SS-OCT using polarization, or the like, in addition to the polarization sensitive SS-OCT.

For example, a first optical detector 121Va and a second optical detector 121Vb of a vertical polarization detector (first channel) 121V detect a vertical polarization component split by polarization beam splitters 360 and 365 and perform the balance detection. A first optical detector 121Ha and a second optical detector 121Hb of a horizontal polarization detector (second channel) 121H detect a horizontal polarization component split by the polarization beam splitters 360 and 365 and perform the balance detection.

What is claimed is:

1. An optical coherence tomography device comprising:
   an SS-OCT optical system which includes a wavelength swept optical source configured to sweep an emission wavelength;
   an optical splitter which is configured to split an interference signal light caused by interference between a measurement light and a reference light into a first interference signal light and a second interference signal light having a phase difference with respect to the first interference signal light;
   a first balance detector which includes a first detector configured to detect the first interference signal light and a second detector configured to detect the second interference signal light, and which is configured to process detection signals from the first detector and the second detectors to perform balance detection;
   a first optical member which is disposed between the optical splitter and one of the first detector and the second detector to generate a fixed pattern noise by one of the first interference signal light and the second interference signal light; and
   a calculation processor which is configured to obtain correction information for correcting a mapping state of a wavenumber component for each sampling point in the first balance detector by calculation based on a signal component corresponding to the fixed pattern noise included in a detection signal output from the first balance detector.

2. The optical coherence tomography device according to claim 1,
   wherein the calculation processor is configured to perform sampling of an interference signal between the measurement light and the reference light in accordance with change of the emission wavelength by the wavelength swept optical source and obtain internal information of an examination object based on the interference signal at each wavelength obtained by sampling.

3. The optical coherence tomography device according to claim 1,
   wherein the calculation processor is configured to correct a phase shift of a spectral signal including the interference signal at each wavelength based on the signal component corresponding to the fixed pattern noise included in the detection signal output from the first balance detector.

4. The optical coherence tomography device according to claim 1,
   wherein the first optical member is disposed such that a front surface and a rear surface thereof vertically intersect with an optical axis.

5. The optical coherence tomography device according to claim 1,
   wherein the first optical member is disposed between the optical splitter and one of the first detector and the second detector, for which a light splitting ratio by the optical splitter is higher.

6. The optical coherence tomography device according to claim 1, further comprising:
   a second balance detector which includes a third detector configured to detect the first interference signal light and a fourth detector configured to detect the second interference signal light, and which is configured to process detection signals from the third detector and the fourth detector to perform balance detection; and
   a second optical member which is disposed between the optical splitter and one of the third detector and the fourth detector to generate a fixed pattern noise by one of the first interference signal light and the second interference signal light.

7. The optical coherence tomography device according to claim 6, wherein
   the calculation processor is configured to obtain correction information for correcting a mapping state of a wavenumber component for each sampling point in the second balance detector by calculation based on a signal component corresponding to the fixed pattern noise included in a detection signal output from the second balance detector.

8. The optical coherence tomography device according to claim 6,
   wherein the first detector and the third detector are used as vertical polarization detectors configured to detect an interference signal having a vertical polarization component, at each wavelength,
   wherein the second detector and the fourth detector are used as horizontal polarization detectors configured to detect an interference signal having a horizontal polarization component, at each wavelength, and
   wherein a polarization property of an examination object is obtained based on the interference signals having the vertical polarization component and the horizontal polarization component, at each wavelength.

9. The optical coherence tomography device according to claim 6,
   wherein the second optical member is disposed such that a front surface and a rear surface thereof vertically intersect with an optical axis.

10. The optical coherence tomography device according to claim 6,
    wherein the second optical member is disposed between the optical splitter and one of the third detector and the fourth detector, for which a light splitting ratio by the optical splitter is higher.

11. The optical coherence tomography device according to claim 1,
    wherein the calculation processor is configured to correct a phase shift of a spectral signal output from the first balance detector using the fixed pattern noise generated by the first optical member.

12. The optical coherence tomography device according to claim 11,
    wherein the calculation processor is configured to correct a mapping state of the wavenumber component for each sampling point in the first balance detector is corrected after correcting the phase shift.

13. The optical coherence tomography device according to claim 1,
    wherein the correction information is for correcting the mapping state of the wavenumber component for each sampling point such that a phase φ(k) of the signal component corresponding to the fixed pattern noise converges in a predetermined acceptable range.

14. The optical coherence tomography device according to claim 1,
wherein the calculation processor is configured to:
obtain a phase φ(k) of the signal component which is output from the first balance detector and corresponds to the fixed pattern noise;
obtain the correction information by calculation, with which the obtained phase φ(k) converges in a predetermined acceptable range;
correct a corresponding relationship between each wavenumber component and each sampling point using the obtained correction information; and
obtain internal information of an examination object using the corrected corresponding relationship.

15. An optical coherence tomography device comprising:
an SS-OCT optical system which includes a wavelength swept optical source configured to sweep an emission wavelength and an optical splitter configured to split a light from the wavelength swept optical source into a measurement light and a reference light;
an optical member which is configured to generate a fixed pattern noise by an interference signal light caused by interference between the measurement light and the reference light;
a detector which is configured to receive a light from the wavelength swept optical source through the optical member as the interference signal light; and
a processor which is configured to obtain internal information of an examination object by processing a spectral signal included in an detection signal output from the detector, the spectral signal including interference signals at each wavenumber; and
wherein the processor is configured to correct a phase shift of the spectral signal based on a signal component included in the detection signal and corresponding to the fixed pattern noise, and
wherein the processor obtains the internal information of the examination object based on the corrected spectral signal.

* * * * *